United States Patent [19]

Brudermueller et al.

[11] Patent Number: 5,334,745
[45] Date of Patent: Aug. 2, 1994

[54] PREPARATION OF 3-AMINOPROPIONITRILES

[75] Inventors: Martin Brudermueller, Mannheim; Tom Witzel, Ludwigshafen; Franz Merger, Frankenthal, all of Fed. Rep. of Germany

[73] Assignee: BASF Aktiengesellschaft, Ludwigshafen, Fed. Rep. of Germany

[21] Appl. No.: 69,129

[22] Filed: May 28, 1993

[30] Foreign Application Priority Data

Jun. 4, 1992 [DE] Fed. Rep. of Germany ........ 4218358

[51] Int. Cl.$^5$ ............................................. C07C 253/30
[52] U.S. Cl. ................................ 558/394; 558/390; 558/408; 558/430; 558/432; 558/433; 558/434; 558/455; 558/452
[58] Field of Search ................ 558/452, 455, 394, 390, 558/430, 408

[56] References Cited

U.S. PATENT DOCUMENTS

| | | | |
|---|---|---|---|
| 1,992,615 | 2/1935 | Hoffmann et al. | 558/452 X |
| 2,965,671 | 12/1960 | Hughes | 558/452 |
| 3,222,402 | 12/1965 | Cooperman | 558/452 X |
| 4,172,091 | 10/1979 | Weber et al. | 558/452 |
| 4,211,725 | 7/1980 | Kluger et al. | 558/452 |
| 4,260,556 | 4/1981 | Kluger et al. | 558/452 X |
| 4,965,362 | 10/1990 | Merger et al. | 558/452 X |
| 4,967,006 | 10/1990 | Carr | 558/452 X |
| 5,070,202 | 12/1991 | Herkes | 558/452 X |

FOREIGN PATENT DOCUMENTS

| | | | |
|---|---|---|---|
| 557368 | 5/1958 | Canada | 558/452 |
| 449297 | of 1991 | European Pat. Off. | |
| 2436651 | 2/1975 | Fed. Rep. of Germany | 558/452 |

OTHER PUBLICATIONS

Mekhtiev et al, Chem. Abstr. 76:126429j (1972).
J. Org. Chem., vol. 27 (1962) pp. 4115–4117.
C. R. hebd. Seances Acad. Sci. Ser. C 266 (1968), pp. 1162–1164.

*Primary Examiner*—Joseph Paul Brust
*Attorney, Agent, or Firm*—John H. Shurtleff

[57] ABSTRACT

3-Aminopropionitriles of the general formula I

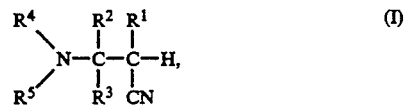

where
$R^1, R^2, R^3, R^4$ and $R^5$ independently of one another are each hydrogen, $C_1$–$C_{20}$-alkyl, $C_1$–$C_8$-aminoalkyl, $C_1$–$C_8$-cyanoalkyl, $C_3$–$C_{20}$-cycloalkyl, $C_7$–$C_{20}$-aralkyl or aryl, are prepared by a process in which an amine of the general formula II

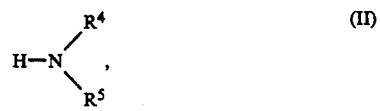

is reacted with an acrylonitrile of the general formula III

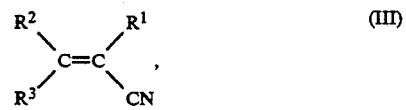

where the substituents have the abovementioned meanings, in a molar ratio of from 0.9:1 to 100:1 over a heterogeneous catalyst at from 40° to 200° C. and from 1 to 350 bar.

7 Claims, No Drawings

PREPARATION OF 3-AMINOPROPIONITRILES

DESCRIPTION

The present invention relates to a novel process for the preparation of 3-aminopropionitriles by reacting ammonia or a primary or secondary amine with an alpha/beta-unsaturated nitrile over a heterogeneous catalyst.

Examples of addition reactions of ammonia and substituted amines with alpha/beta-unsaturated nitriles according to EP-A-449 297 are the addition reaction of ammonia with 2-pentenenitrile in the presence of from 15 to 60% by weight of water and the addition reaction of ethylenediamine with 2-pentenenitrile in the presence of 5 equivalents of water. Water serves as a proton-transfer catalyst in the addition reaction. SU-A-327 185 discloses the addition reaction of aqueous ammonia with methacrylonitrile.

The stated processes have the disadvantage that, when water is used as homogeneous catalyst, undesirable hydrolysis of the nitrile-products may result in lower yields.

J. Org. Chem. 27 (1962), 4115-4117 discloses the addition reaction of fatty amines with acrylonitrile in the presence of ion exchangers, such as Dowex ® 50W or Duolite ® C-63, while C.R. hebd. Seances Acad. Sci. Set. C 266 (1968) describes Amberlyst 15 as a catalyst.

However, the general advantages of heterogeneous catalysis when ion exchangers are used as a catalyst are greatly restricted by the limited thermal stability of the polymers and their declining catalytic activity on repeated use.

It is an object of the present invention to remedy the abovementioned disadvantages.

We have found that this object is achieved by a novel and improved process for the preparation of 3-aminopropionitriles of the general formula I

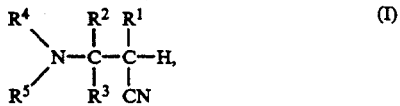

where,
$R^1, R^2, R^3, R^4$ and $R^5$ independently of one another, are each hydrogen, $C_1$–$C_{20}$-alkyl, $C_1$–$C_8$-aminoalkyl, $C_1$–$C_8$-cyanoalkyl, $C_3$–$C_{20}$-cycloalkyl, $C_7$–$C_{20}$-aralkyl or aryl,
wherein an amine of the general formula II

is reacted with an acrylonitrile of the general formula III

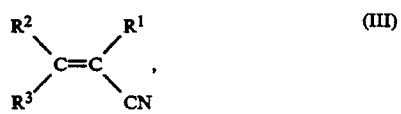

where the substituents have the abovementioned meanings, in a molar ratio of from 0.9:1 to 100:1 over a heterogeneous catalyst at from 40° to 200° C. and from 1 to 350 bar.

The novel process can be carried out as follows:
The reaction can be carried out batchwise, or, preferably, continuously at from 40° to 200° C., preferably from 80° to 160° C., and from 1 to 350 bar, preferably at from 1 to 150 bar when the primary and secondary amines are used and at from 150 to 250 bar when ammonia is used, it being possible to employ any conventional reactor, such as a stirred reactor, a tubular reactor or a stirred cascade. The preferred continuous process can be carried out at from 40° to 160° C. and from 1 to 150 bar, preferably from 40° to 140° C. and from 10 to 100 bar.

Ammonia and the primary or secondary amines II are usually used in anhydrous form, in essentially anhydrous form or with the water content usual in commercial material, but amines having water contents of from >0.1–10% by weight may also be employed.

The amine II and alpha,beta-unsaturated nitrile III are used in a molar ratio of from 0.9:1 to 100:1, preferably from 1:1 to 50:1, particularly preferably from 1.02:1 to 15:1. Ammonia or amine which has not been converted in the reaction can be separated off and recycled to the reaction (circulation procedure).

In general no solvent is used; however, inert solvents, for example ethers such as dibutyl ether, tetrahydrofuran or dimethyl ether, or hydrocarbons, such as cyclohexane, benzene or toluene, but particularly preferably excess amine III may be used, in amounts of from 0 to 500, preferably from 50 to 200, % by weight, based on the alpha,beta-unsaturated nitrile.

In the reaction, a space velocity of from 0.05 to 50, preferably from 0.1 to 20, g of alpha, beta-unsaturated nitrile III per g of catalyst per hour is advantageously maintained.

Suitable heterogeneous catalysts apart from ion exchangers are in particular acidic and/or basic or amphoteric oxides of elements of the second, third and fourth main groups, in particular various modifications of $Al_2O_3$ and $SiO_2$ in the form of silica gel, kieselguhr, quartz or mixtures thereof, and of the first to sixth subgroups of the Periodic Table of Elements, and lanthanides or mixtures thereof. Other advantageous catalysts are titanium oxide, zirconium oxide, vanadium oxide, niobium oxide, boron oxides, chromium oxides, molybdenum oxides, tungsten oxides or mixtures thefor. Mixtures of these oxides with alumina are also suitable for this reaction. Further catalysts for the novel process are zeolites, phosphates or heteropoly acids.

In the compounds I, II and III, $R^1$, $R^2$, $R^3$, $R^4$ and $R^5$ independently of one another are each:
hydrogen,
$C_1$–$C_{20}$-alkyl, such as methyl, ethyl, n-propyl, isopropyl, n-butyl, isobutyl, sec-butyl, tert-butyl, n-pentyl, isopentyl, tert-amyl, n-hexyl, iso-hexyl, n-heptyl, isoheptyl, n-octyl or isooctyl, preferably $C_1$–$C_4$-alkyl such as methyl, ethyl, n-propyl, isopropyl, n-butyl, iso-butyl, sec-butyl or tert-butyl, particularly preferably methyl and ethyl,
$C_1$–$C_8$-aminoalkyl, such as 2-aminoethyl or 3-aminopropyl,
cyanoalkyl wherein alkyl has 1 to 8 carbon atoms, such as 2-cyanoethyl,
$C_3$–$C_{20}$-cycloalkyl, preferably $C_3$–$C_8$-cycloalkyl, such as cyclopropyl, cyclobutyl, cyclopentyl, cyclohexyl, cycloheptyl or cyclooctyl, particularly preferably cyclopentyl or cyclohexyl, $C_7$–$C_{20}$-aralkyl, preferably $C_7$–$C_{12}$-phenylalkyl, such as benzyl, 1phenethyl, 2-phenethyl, 1-phenylpropyl, 2-phenylpropyl, 3-phenylpropyl, 1-phenylbutyl, 2- phenylbutyl, 3-phenylbutyl or 4-phenylbutyl, particularly preferably benzyl, 1-phenethyl or 2-phenethyl, or aryl such as phenyl, 1-naphthyl, 2-naphthyl, 1-anthranyl, 2-anthranyl or 9-anthranyl, preferably phenyl, 1-naphthyl or 2-naphthyl, particularly preferably phenyl.

The aminopropionitriles of the general formula I which can be prepared by the novel process are intermediates for the preparation of diamines, aminocarboxylic acids or aminocarboxamides.

EXAMPLES

The addition reaction of ammonia or primary and secondary amines with alpha,beta-unsaturated nitriles was carried out in a pressure apparatus (max. 100 bar) which consists of two calibrated metering pumps for separate metering of amine and nitrile, a mixing zone for homogenizing the reactants, a catalyst-filled heated tubular reactor and a let-down apparatus as well as a condenser. The reacted mixture is cooled and analyzed by gas chromatography.

The Examples are shown in Tables 1 to 4.

The following abbreviations are used:

RT—Residence time of the reaction mixture, based on the reactor volume

Mono—Monoadduct (1 equivalent of amine/1 equivalent of nitrile

Di—Bisadduct (1 equivalent of amine/2 equivalents of nitrile)

TABLE 1

| | Substituted nitriles/methylamine | | | | | | | | |
|---|---|---|---|---|---|---|---|---|---|
| | Molar ratio [mol/mol] | | Temp. | RT** | Reacted mixture in % by area | | | | |
| Nitrile | Amine | Nitrile | [°C.] | [min] | Nitrile | Amine* | "Mono" | "Di" | Others |
| Catalyst: $Al_2O_3/SiO_2$ (80/20) | | | | | | | | | |
| Cinnamonitrile | 01.1 | 2.0 | 120 | 20 | 57.8 | 04.0 | 35.0 | 01.3 | 01.9 |
| Cinnamonitrile | 11.0 | 1.0 | 130 | 30 | 00.9 | 15.9 | 44.7 | 36.5 | 01.2 |
| 3-Methylcrotononitrile | 11.0 | 1.0 | 130 | 30 | 43.9 | 12.3 | 43.3 | — | — |
| 2-Methylcrotononitrile | 11.0 | 1.0 | 150 | 30 | 42.2 | 19.7 | 32.4 | — | 05.7 |
| Crotononitrile | 11.0 | 1.0 | 130 | 30 | sp. | 15.0 | 83.0 | — | 02.0 |
| 2-Pentenenitrile | 15.0*** | 1.0 | 130 | 90 | 13.4 | 06.1 | 78.1 | — | 02.4 |
| Comparative experiments without catalyst! | | | | | | | | | |
| Cinnamonitrile | 11.0 | 1.0 | 130 | 30 | 63.0 | 04.5 | 29.0 | 00.0 | 00.0 |
| 3-Methylcrotononitrile | 11.0 | 1.0 | 130 | 30 | 84.1 | 14.2 | 01.5 | 00.0 | 00.2 |
| Crotononitrile | 11.0 | 1.0 | 130 | 30 | 09.6 | 14.8 | 75.6 | 00.0 | 00.0 |

*volatilization of amine differs!
**calculated on empty tube!
***ammonia

TABLE 2

| | Acrylonitrile/substituted amines | | | | | | | | | |
|---|---|---|---|---|---|---|---|---|---|---|
| | Molar ratio [mol/mol] | | Temp. | | Reacted mixture in % by area | | | | | |
| Amine | Amine | Nitrile | [°C.] | RT** [min] | Nitrile | Amine* | "Mono" | "Di" | Others | $H_2O$ [% by weight] |
| Catalyst: $Al_2O_3/SiO_2$ (80/20) | | | | | | | | | | |
| Methylamine | 1.10 | 2.0 | 60 | 10 | | 18.3 | sp | 85.6 | 00.0 | 0.30 |
| Dimethylamine | 1.05 | 1.0 | 60 | 10 | sp | 01.9 | 97.8 | — | 00.0 | 0.10 |
| Diethylamine | 1.03 | 1.0 | 120 | 15 | 00.3 | 07.6 | 92.1 | — | 00.0 | 0.04 |
| Cyclohexylamine | 1.03 | 1.0 | 100 | 15 | 02.7 | 07.7 | — | 89.5 | 00.0 | 0.25 |
| tert-Butylamine | 1.03 | 1.0 | 120 | 15 | 10.9 | 07.8 | 81.3 | — | 00.0 | 0.40 |
| Aniline | 1.10 | 1.0 | 120 | 20 | 24.2 | 41.8 | 34.0 | — | 00.0 | — |
| Comparative experiments without catalyst! | | | | | | | | | | |
| Cyclohexylamine | 1.03 | 1.0 | 120 | 15 | 32.9 | 47.5 | 19.6 | — | 00.0 | 0.25 |
| Diethylamine | 1.03 | 1.0 | 120 | 15 | 37.7 | 46.8 | 16.1 | — | 00.0 | 0.04 |
| tert-Butylamine | 1.03 | 1.0 | 120 | 15 | 45.3 | 45.5 | 09.6 | — | 00.0 | 0.40 |

*volatilization of low-boiling amines differs!
**based on empty tube!

TABLE 3

| Acrylonitrile/Diethylamine - Variation of the reaction temperature | | | | | | | |
|---|---|---|---|---|---|---|---|
| Molar ratio [mol/mol] | | Temp. | RT* | Reacted mixture in % by area | | | |
| Nitrile | Amine | [°C.] | [min] | Nitrile | Amine | Adduct | Others |
| Catalyst: $Al_2O_3/SiO_2$ (80/20) | | | | | | | |
| 1.00 | 1.03 | 40 | 15 | 21.50 | 19.75 | 58.75 | 00.00 |
| 1.00 | 1.03 | 60 | 15 | 12.50 | 11.10 | 76.40 | 00.00 |
| 1.00 | 1.03 | 80 | 15 | 06.80 | 05.80 | 87.30 | 00.00 |
| 1.00 | 1.03 | 100 | 15 | 04.00 | 02.90 | 93.10 | 00.00 |
| 1.00 | 1.03 | 120 | 15 | 01.10 | 02.10 | 96.50 | 00.00 |

*based on empty tube!

TABLE 4

| Acrylonitrile/Cyclohexylamine - Variation of the catalyst | | | | | | | | |
|---|---|---|---|---|---|---|---|---|
| Catalyst** | Molar ratio [mol/mol] | | Temp. | RT+ | Reacted mixture in % by area | | | $H_2O$ Content |
| | Nitrile | Amine | [°C.] | [min] | Nitrile | Amine | Adduct | |
| $Al_2O_3/SiO_2$ (80/20) | 1.00 | 1.03 | 120 | 15 | 01.20 | 06.20 | 92.60 | 00.37 |

TABLE 4-continued

Acrylonitrile/Cyclohexylamine - Variation of the catalyst

| Catalyst** | Molar ratio [mol/mol] Nitrile | Amine | Temp. [°C.] | RT+ [min] | Reacted mixture in % by area Nitrile | Amine | Adduct | H₂O Content |
|---|---|---|---|---|---|---|---|---|
| TiO₂ | 1.00 | 1.03 | 120 | 15 | 09.20 | 17.30 | 18.30 | 00.37 |
| SiO₂ | 1.00 | 1.03 | 120 | 15 | 00.50 | 04.70 | 93.80 | 00.37 |
| MgO | 1.00 | 1.03 | 120 | 15 | 13.70 | 25.50 | 60.80 | 00.37 |
| CeO₂ | 1.00 | 1.03 | 120 | 15 | 12.40 | 22.30 | 65.30 | 00.37 |
| ZrO₂ | 1.00 | 1.03 | 120 | 15 | 13.10 | 22.60 | 70.60 | 00.37 |
| Zeolite/ZSM-5 | 1.00 | 1.03 | 120 | 15 | 10.40 | 18.40 | 71.20 | 00.37 |
| — | 1.00 | 1.03 | 120 | 15 | 32.90 | 47.50 | 19.60 | 00.37 |

*based on empty tube!
**1-2 mm particle size

We claim:

1. A process for the preparation of a 3-aminopropionitrile of the formula

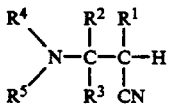

wherein $R^1$, $R^2$, $R^3$, $R^4$ and $R^5$, independently of one another, are each hydrogen, $C_1$-$C_{20}$-alkyl, $C_1$-$C_8$-aminoalkyl, cyano-$C_1$-$C_8$-alkyl, $C_3$-$C_{20}$-cycloalkyl, $C_7$-$C_{20}$-aralkyl or $C_6$-$C_{14}$-aryl, with the proviso that each aryl group has a carbocyclic structure, which process comprises:

reacting an amine of the formula

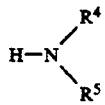

with an acrylonitrile of the formula

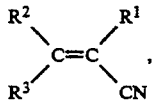

wherein the substituents have the above-mentioned meanings, in a molar ratio of from 0.9:1 to 100:1 at a temperature of from 40° to 200° C. and a pressure of from 1 to 350 bar over a heterogeneous catalyst selected from the group consisting of oxides of the second, third or fourth main groups or of the third to sixth subgroups of the Periodic Table of Elements, acidic zeolites and mixtures thereof.

2. A process as claimed in claim 1, wherein said catalyst is selected from the group consisting of aluminum oxide, silicon dioxide and mixtures thereof.

3. A process as claimed in claim 1, wherein said catalyst is selected from the group consisting of the oxides of titanium, zirconium, vanadium, niobium, boron, chromium, molybdenum, tungsten and mixtures thereof.

4. A process as claimed in claim 1, wherein the catalyst is an acidic zeolite.

5. A process as claimed in claim 1, wherein the reaction is carried out at from 80° to 160° C.

6. A process as claimed in claim 1, wherein the reaction with a primary or secondary amine is carried out at from 1 to 150 bar.

7. A process as claimed in claim 1, wherein the reaction with ammonia is carried out at from 150 to 230 bar.

* * * * *